Figure 1:
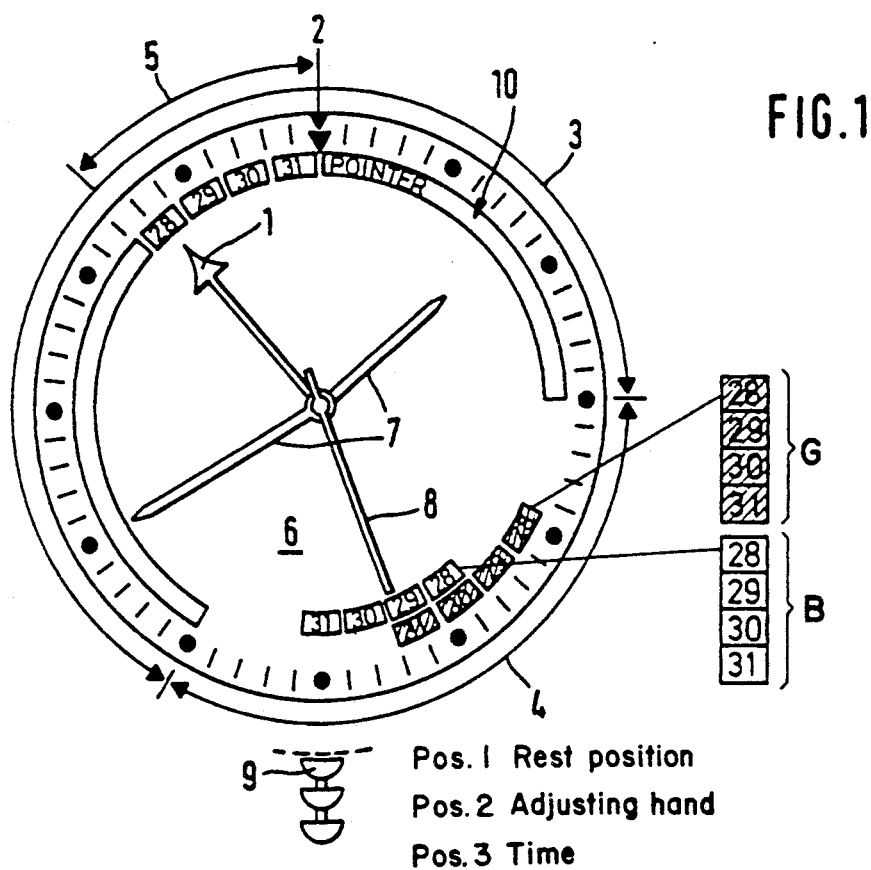

United States Patent [19]

Riesen

[11] Patent Number: 5,058,084
[45] Date of Patent: Oct. 15, 1991

[54] CLOCK HAVING A DEVICE FOR PLANNING THE SEX OF A CHILD ACCORDING TO THE TIME SELECTION METHOD

[75] Inventor: Heinz Riesen, Büsserach, Switzerland

[73] Assignee: B-Line AG, Heimenhausen, Switzerland

[21] Appl. No.: 570,862

[22] Filed: Aug. 21, 1990

[30] Foreign Application Priority Data

Aug. 21, 1989 [CH] Switzerland ................ 3024/89

[51] Int. Cl.⁵ .............. G04B 47/00; G04B 19/24; A61B 10/00
[52] U.S. Cl. ................................ 368/10; 368/28; 128/738
[58] Field of Search ................ 368/10, 28–30, 368/37–40; 128/738; 235/88 RC

[56] References Cited

U.S. PATENT DOCUMENTS

| | | | |
|---|---|---|---|
| 3,964,674 | 6/1976 | Van der Gaast | 235/88 RC |
| 4,151,831 | 5/1979 | Lester | 128/736 |
| 4,410,797 | 10/1983 | Hatzold | 235/69 |
| 4,527,906 | 7/1985 | Jezbera | 368/107 |
| 4,788,984 | 12/1988 | Marsik | 128/738 |

Primary Examiner—Vit W. Miska
Attorney, Agent, or Firm—Ralph W. Selitto, Jr.

[57] ABSTRACT

In a clock, a device for planning the sex of a child according to the time selection method exhibits differently marked display sections (3, 4 and 5), relative to a display starting position (2), for labeling the days of fertility and the days of infertility in a cycle and a limited cycle variation range. Within the display section for the days of fertility (4), clearly distinguishably marked day position fields (G and B) are provided which, for cycle lengths of 27 to 30 days, serve as an indication of the days of probability for conceiving a boy or a girl. The counting and display of the days of probability by the cycle pointer (1) occurs from the respective first day of a new menstruation. Correspondingly, the display element (1, 11) can be adjusted to the starting position (2).

12 Claims, 3 Drawing Sheets

Pos. 1 Rest position
Pos. 2 Adjusting hand
Pos. 3 Time

CLOCK HAVING A DEVICE FOR PLANNING THE SEX OF A CHILD ACCORDING TO THE TIME SELECTION METHOD

DESCRIPTION

The invention relates to a clock having a device according to the preamble of patent claim 1.

The time selection method mentioned there is illustrated inter alia in the book by Dr. Otfried Hatzold "Wunschkind Sohn oder Tochter" [Planned Child—Son or Daughter], Munich 1985 (4th edition) and the research report JSBN No. 3-89 162/003/9 by the same author. A calculation table for birth planning according to this method is known from DE 2,949,087 A1.

In the known calculation, use is made of the knowledge that the time of conception within the cycle is decisive for the sex of the child for the following reasons: the female egg is neutral in terms of sex and the male-determining sperms swim faster to the egg than the female-determining sperms, but the latter remain capable of fertilization for longer, namely for approximately 2 days. In the case of sexual intercourse 2 days prior to ovulation, a girl can therefore be expected with high probability since the male-determining sperms do not generally survive this period and only the female-determining sperms reach fertilization. If, in contrast, sexual intercourse takes place on the day of ovulation, the probability of fertilization by a male-determining sperm is high since the latter meet the egg first due to their faster mobility.

In the course of a research project described in the abovementioned book, the application of this knowledge has resulted in a success rate of approximately 90%. However, in order to achieve such a high success rate, it is, of course, a prerequisite to be able to determine the day of ovulation with high probability in each new cycle In this case, recording as many cycle patterns as possible from the past, in particular during the last 12 months, can give a degree of certainty with regard to expected variations since the day of the previous ovulation has, with high regularity, an interval of 15 days from the first day of each new menstruation. The cycle variations, which can be established with the day of commencement of menstruation, consequently allow a very reliable conclusion to be drawn concerning the corresponding shift of the day on which the last ovulation took place. The smaller the established cycle variations are, the greater the forecast probability is. An uncertainty in the calculation, occurring not infrequently in the past even in professional circles, can today be ruled out by careful application of the abovementioned calculation table.

Clocks are already known, for example BE-A-729,841, which allow the dates of a menstrual cycle to be read off, taking cycle variations into consideration. It is also known to use in a clock different colors or pictorial symbols to make different periods visible within a menstrual cycle (CH-A-294,405). However, these known clocks are not suitable for planning the sex of a child.

The object of the invention is to provide a clock of the type mentioned at the beginning which gives an overview at any time within a determined cycle variation range both of the days of fertility and the days of infertility and of the period of ovulation and the probability of conception for girls or boys and which does not require any calculations by the user.

This object is achieved in particular by the features defined in the characterizing part of patent claim 1.

Further developments of the subject matter of the invention emerge from the dependent patent claims.

In the clock according to the invention, the abovementioned calculation errors are ruled out with certainty by the fact that the position fields for the respective days of conception are numbered according to the first day of the new menstruation and not according to the cycle length.

The clock according to the invention takes monthly cycle variations of four days into consideration. The corresponding cycle lengths are between 27 and 30 days; these are represented by the position fields for the 28th, the 29th, the 30th and the 31st days.

An easily visible arrangement of the position fields is achieved in the clock according to the invention by the fact that the position fields of all "Girl" days are marked corresponding to the cycle length separately from or highlighted with respect to those of all "Boy" days corresponding to the cycle duration. These markings are advantageously arranged in mutually concentrically offset segments of circles.

Since, according to a type of embodiment of the invention, the position fields of the cycle variation display area occupy the last four days before the starting position and are labeled with the correspondingly increasing position numbers, it is readily possible on the first day of the new cycle to read off directly the relevant position field to record the cycle length, to note the field number and to return the display to its starting position again.

Figure 2:
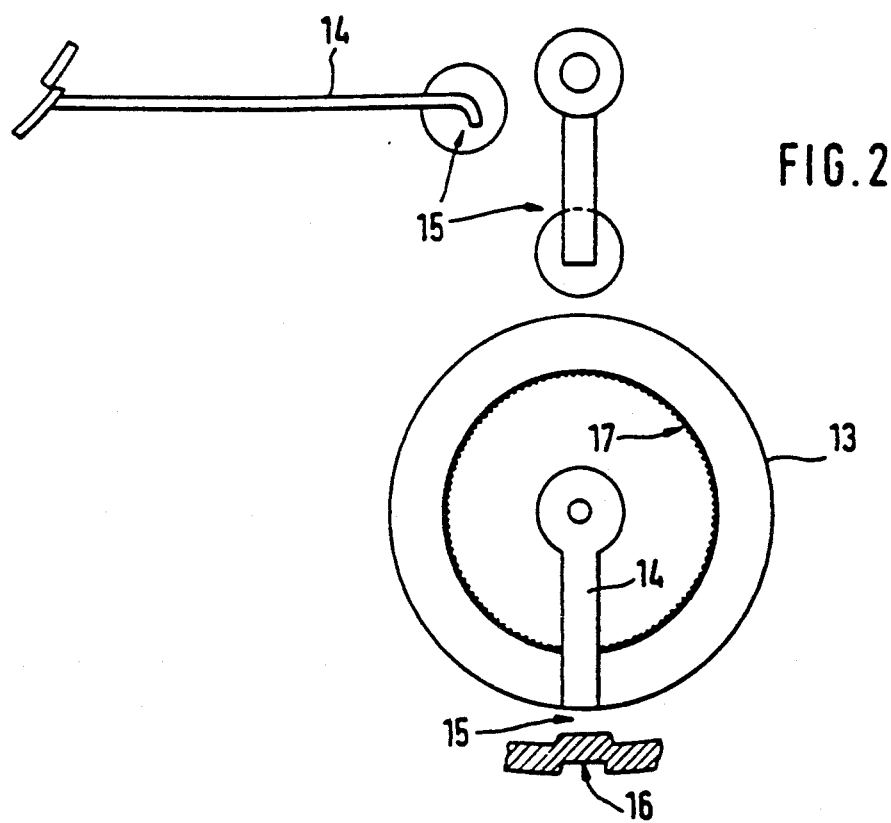
Figure 3:
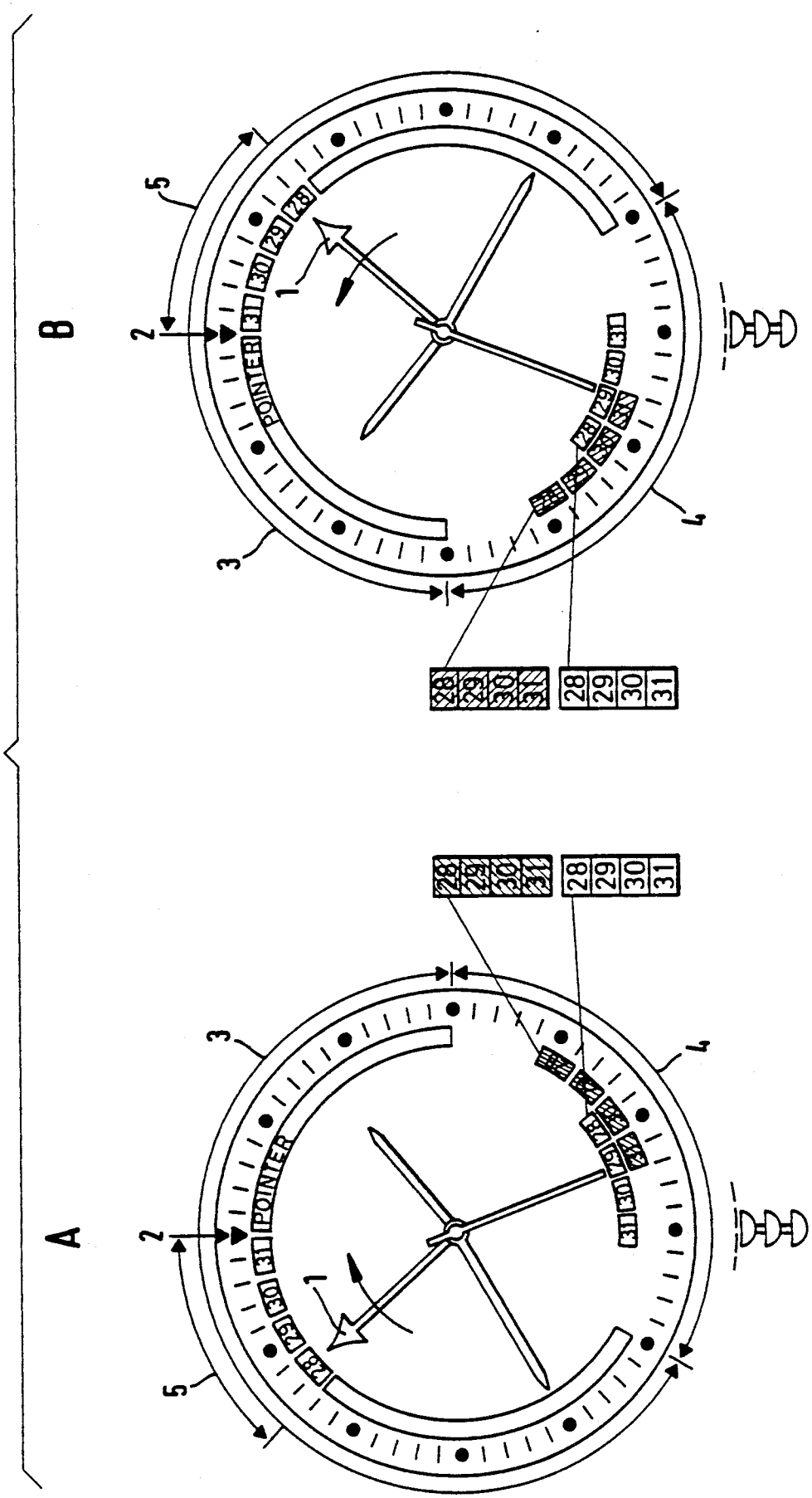
Figure 4:
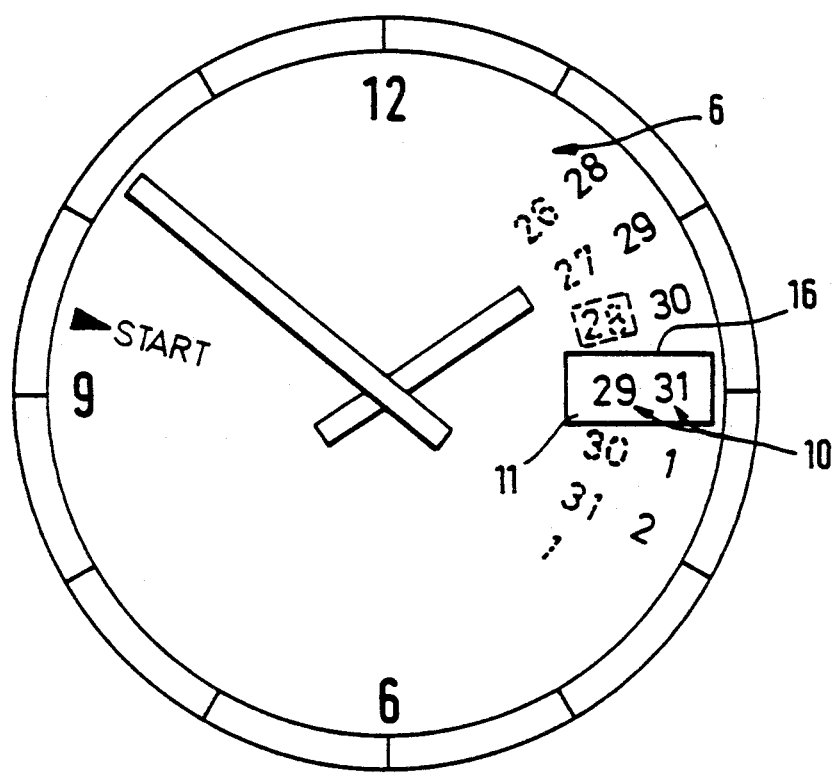

Further features and advantages of the invention result from the description of exemplary embodiments which follows, with reference to drawings, in which:

FIG. 1 shows a diagrammatic illustration of a clock designed according to the features of the invention having a cycle pointer display, FIG. 2 shows a diagrammatic illustration of drive details of a clock according to FIG. 1, FIG. 3 shows two illustrations of clocks according to FIG. 1, having a cycle pointer display moving clockwise in (A) and moving counterclockwise in (B) and FIG. 4 shows a diagrammatic illustration of a further embodiment of a clock designed according to the features of the invention and having a date window display.

The clock according to FIG. 1 has a face 6, a pair of minute and hour hands 7, a second hand 8 and a display element 1 in the form of a cycle pointer. Situated behind the visible face area there is a precise clock movement of conventional construction. The face 6 is provided with a customary hour and minute division, the 12 o'clock position being characterized particularly by a triangle symbol. Situated opposite the 6 o'clock position there is an adjusting wheel 9 which can be displaced between the three positions illustrated, position 1 being the rest position, position 2 serving for setting and adjusting the cycle pointer 1 and position 3 for setting the time.

Situated concentrically within the hour and minute division there is an annular display area 10 which is subdivided into the following sections: a section 3 which marks the days of infertility in a cycle, a section 4 which indicates the days of fertility and a section 5 to display a cycle variation range. Starting from a starting position 2 corresponding to the 12 o'clock position of the clock, the display area 10 is subdivided into 31 day position fields, over which the cycle pointer 1 passes in 30 steps, like a date pointer over a month, and, with the 31st step, jumps back to the starting position 2. In the illustrated embodiment, cycle variations of four days are taken into consideration (corresponding to cycle lengths of 27 to 30 days).

Situated within the section 4 which indicate the days of fertility there are two mutually concentrically offset section segments G and B. Each segment is subdivided into four day position fields designated as 28, 29, 30 and 31 corresponding to the cycle variation range and the two segments overlap by two day positions. The days defined as G are the "Girl" days corresponding to the cycle duration and those designated as B the "Boy" days. Situated between these section segments G and B and the ends of the section 3 there are in each case two day positions as a safety margin. In practical construction, the "Girl" days can be colored pink and the "Boy" days can be colored blue.

Knowledge of the individual cycle pattern is decisive for the application of the clock for determining the sex of a child. If, for example, during the last 12 cycles (without the pill having been taken) corresponding records were kept which show that there is a cycle variation range within the abovementioned variation range, the clock can be used at the beginning of the next menstruation. For this purpose, the cycle pointer 1 is simply set at the starting position 2 on the first day of the new cycle. When, for example, in a cycle duration of 28 day positions resulting from the records, the pointer reaches the field G with the number 28 in section 4, there is an increased probability of conceiving a girl on the day in question. This applies accordingly for the cycle duration according to the other numbers and for the day positions at B for boys.

When the pointer on its continued path reaches the cycle variation range 5 again and menstruation is supposed to begin, for example, at the day position 30 of this range, this position number is to be noted and the cycle pointer 1 is to be set at its starting position 2 again.

In the case of cycle variations within the specified range, if a girl is desired that field G is to be selected as conception day which corresponds to the lowest position number noted and, if a boy is desired, in contrast, the field B with the highest position number noted. Furthermore, it is important that, within the section 4 for the days of fertility, if a girl is desired no intercourse without precautions may take place after the conception day and, if a boy is desired, before the conception day.

FIG. 2 shows an annular disk 13 which has the appearance of a date display disk. Provided on the inside diameter of this disk there is a driving toothed wheel 17 of customary construction, via which the disk 13 can be stepped forward daily by the clock movement (not illustrated). In order to transmit this drive movement to the cycle pointer 1, a drive digit 14 is provided which, with its end 15 of bent construction, engages in an edge notch 16 of the disk. When the disk 13 is rotated by means of the positioning knob or by stepping by the clock movement, a corresponding swiveling of the digit 14 is effected which, in turn, moves on the number pointer 1 connected to it. By means of this simple type of drive, the device according to the invention can be adapted to conventional clocks without large-scale production conversions.

FIG. 3 shows two display sections 3, 4 and 5, constructed in mirror image, for a cycle pointer constructed so as to rotate to the right (A) and to rotate to the left (B).

In FIG. 4, the sections 3, 4, 5, B and G provided on the face 6 in FIGS. 1 and 3 are provided on a date display disk 15. Instead of the cycle pointer, a window 16 is provided which makes the respective position number visible.

I claim:

1. A clock having a device for planning the sex of a child according to the time selection method, having an adjustable display element (1, 11) driven by the clock movement, which display element designates each predetermined day position within a display area (10) in a similar way to a date display, the display area, relative to a display starting position (2), comprising differently marked display sections (3, 4 and 5) to label the days of fertility and the days of infertility in a cycle and a limited cycle variation range, wherein clearly distinguishably marked day position fields (G and B) are provided within the display section for the days of fertility (4) at different intervals of days—stipulated according to the time selection method—from the starting position (2), which day position fields, for cycle lengths of 27 to 30 days, serve as an indication of the days of probability for conceiving a boy or a girl, it being possible for the display element (1, 11) to be adjusted to the starting position (2) for the counting and display, always occurring from the first day of a new cycle, of the days of probability.

2. The clock as claimed in claim 1, wherein, within the display sections (3, 4 and 5), the day position fields for the "Girl" days (G) are marked corresponding to the respective cycle length separately from or highlighted with respect to those of the "Boy" days (B) likewise corresponding to the cycle duration.

3. The clock as claimed in claim 2, wherein the said day position fields (G and B) are arranged in the form of differently colored arcs of a segment of a circle which are mutually concentrically offset.

4. The clock as claimed in one of claims 1 to 3, wherein the day position fields of the cycle variation display area (5) occupy the last four day fields before the starting position (2) and are labeled with position numbers (28, 29, 30 and 31) which increase in the drive direction of the display element (1, 11).

5. The clock as claimed in claim 4, having a concentrically peripheral drive for the date display, wherein a concentrically central drive (14, 15) of a cycle pointer (1) is derived from the concentrically peripheral drive (13, 16 and 17) for the date display.

6. The clock as claimed in claim 4, having a date display disk and an associated drive, of which date numbers positioned concentrically on the date display disk are each visible through a window (16) in a face (6), wherein the different display sections (3, 4 and 5) are highlighted relative to each other by different coloring and/or shaping of the date numbers and/or of their background.

7. The clock as claimed in claim 4, wherein the display element (1, 11) is driven either clockwise or in the opposite direction, and wherein the display area (10) is correspondingly constructed in mirror image with regard to the starting position (2).

8. The clock as claimed in one of claims 1 to 3, having a concentrically peripheral drive for the date display, wherein a concentrically central drive (14, 15) of a cycle pointer (1) is derived from the concentrically peripheral drive (13, 16 and 17) for the date display.

9. The clock as claimed in one of claims 1 to 3, having a date display disk and an associated drive, of which date numbers positioned concentrically on the date display disk are each visible through a window (16) in a face (6), wherein the different display sections (3, 4 and 5) are highlighted relative to each other by different coloring and/or shaping of the date numbers and/or of their background.

10. The clock as claimed in one of claims 1 to 3, wherein the display element (1, 11) is driven either clockwise or in the opposite direction, and wherein the display are (10) is correspondingly constructed in mirror image with regard to the starting position (2).

11. The clock as claimed in claim 5, wherein the display element (1, 11) is driven either clockwise or in the opposite direction, and wherein the display area (10) is correspondingly constructed in mirror image with regard to the starting position (2).

12. The clock as claimed in claim 6, wherein the display element (1, 11) is driven either clockwise or in the opposite direction, and wherein the display area (10) is correspondingly constructed in mirror image with regard to the starting position (2).

* * * * *